United States Patent [19]

Elliott et al.

[11] Patent Number: 5,011,682

[45] Date of Patent: Apr. 30, 1991

[54] HYPOPHOSPHITE-CONTAINING COTELOMERS AS ANTITARTAR AGENTS

[75] Inventors: David L. Elliott, Hawthorne; Catherine L. Howie, Parsippany, both of N.J.; Peter G. Montague, Rugby, England

[73] Assignee: Conopco, Inc., New York, N.Y.

[21] Appl. No.: 510,651

[22] Filed: Apr. 18, 1990

[51] Int. Cl.$^5$ .................. A61K 7/16; A61K 7/18
[52] U.S. Cl. ...................... 424/52; 424/49; 424/57
[58] Field of Search ................ 424/49, 52, 59

[56] References Cited

U.S. PATENT DOCUMENTS

| | | |
|---|---|---|
| 2,957,931 | 10/1960 | Hamilton et al. . |
| 3,062,792 | 11/1962 | McConnell et al. . |
| 3,429,963 | 2/1969 | Shedlovsky .................. 424/56 |
| 3,576,793 | 4/1971 | Carroll et al. . |
| 3,934,002 | 1/1976 | Haefele ........................ 424/54 |
| 4,025,616 | 5/1977 | Haefele ........................ 424/52 |
| 4,052,160 | 10/1977 | Cook et al. . |
| 4,110,083 | 8/1978 | Benedict ...................... 424/49 |
| 4,138,477 | 2/1979 | Gaffar . |
| 4,157,387 | 6/1979 | Benedict ...................... 424/49 |
| 4,183,914 | 1/1980 | Gaffar et al. .................. 424/48 |
| 4,207,405 | 6/1980 | Masler, III et al. . |
| 4,446,028 | 5/1984 | Becker . |
| 4,515,772 | 5/1985 | Parran, Jr. et al. ........... 424/57 |
| 4,534,866 | 8/1985 | Becker . |
| 4,590,066 | 5/1986 | Parran, Jr. et al. ........... 424/52 |
| 4,627,977 | 12/1986 | Gaffar et al. .................. 424/52 |
| 4,661,341 | 4/1987 | Benedict et al. .............. 424/48 |
| 4,681,686 | 7/1987 | Richardson et al. .......... 210/699 |
| 4,684,518 | 8/1987 | Parran, Jr. et al. ........... 424/52 |
| 4,806,340 | 2/1989 | Gaffar et al. .................. 424/52 |
| 4,806,342 | 2/1989 | Gaffar et al. .................. 424/52 |
| 4,808,400 | 2/1989 | Gaffar et al. .................. 424/52 |
| 4,808,401 | 2/1989 | Gaffar et al. .................. 424/52 |
| 4,842,847 | 6/1989 | Amjad . |
| 4,877,603 | 10/1989 | Degenhardt et al. .......... 424/57 |
| 4,892,724 | 1/1990 | Amjad . |
| 4,892,725 | 1/1990 | Amjad . |

FOREIGN PATENT DOCUMENTS

| | | |
|---|---|---|
| 0341662 | 11/1989 | European Pat. Off. . |
| 1458235 | 12/1976 | United Kingdom . |
| 1572406 | 7/1980 | United Kingdom . |
| 2089807 | 6/1982 | United Kingdom . |
| 2139635 | 11/1984 | United Kingdom . |

*Primary Examiner*—Shep K. Rose
*Attorney, Agent, or Firm*—Milton L. Honig

[57] ABSTRACT

A method and composition for controlling tartar formation in the mouth is reported based upon low molecular weight polymers. These polymers are formed from a mixture of mono- and di- carboxylic vinyl monomers reacted with hypophosphite groups. Particularly effective are phosphorus containing acrylate/maleate polymers of weight averaged molecular weight ranging from about 400 to 5000.

17 Claims, No Drawings

HYPOPHOSPHITE-CONTAINING COTELOMERS AS ANTITARTAR AGENTS

BACKGROUND OF THE INVENTION

1. Field of the Invention

The invention relates to new antitartar agents, dentifrice compositions containing these agents and use of such compositions to control tartar accumulation on teeth. 2. The Related Art Tartar, known also as calculus, is a hard, mineralized deposit which forms around teeth. This formation arises from deposition of crystals of calcium phosphate in the pellicle and the extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective antitartar agents.

Soluble inorganic pyrophosphate salts have over the last few years set the commercial standard as tartar control agents. This technology has been reported by Parran, Jr. et al. in a series of patents including U.S. Pat. No. 4,590,077, U.S. Pat. No. 4,515,772 and U.S. Pat. No. 4,684,518.

Anionic polymers, especially carboxylate group functionalized polymers, have been widely reported as effective against calculus. For example, typically, low molecular weight anionic materials of high charge density are preferred in most of the prior art. U.S. Pat. No. 4,661,341 (Benedict et al.) discloses the use of low molecular weight polyacrylic acids (MW range 3500 to 7500) in dental compositions. U.S. Pat. No. 3,429,963 (Shedlovsky) teaches use of maleate-containing copolymers and vinyl sulfonates in toothpaste. U.S. Pat. No. 4,183,914 (Gaffar et al.) reports use of polymaleates as anticalculus agents. The materials of Gaffar et al. cannot be obtained above molecular weight 1,000 and often have low purity in available commercial samples. High levels of impurities result in polymeric materials of poor appearance, taste and inadequate safety.

Commercially most significant has been the use of synthetic, linear anionic polymers of higher molecular weight in combination with the inorganic pyrophosphates. This technology derives from work done by Gaffar et al. reported in a series of patents including U.S. Pat. No. 4,627,977, U.S. Pat. No. 4,806,340, U.S. Pat. No. 4,806,342, U.S. Pat. No. 4,808,400 and U.S. Pat. No. 4,808,401. Anionic polymers described therein were found to inhibit the action of pyrophosphatase in the mouth and therefore allowing greater efficacy of the inorganic pyrophosphate. The commercially operative polymer is a methyl vinyl ether/maleic anhydride copolymer, available under the GAF trademark Gantrez.

Organic phosphonic acid derivatives, some in polymeric form, have been disclosed in U.S. Pat. No. 3,934,002 (Haefele). EP 0 341 662 (Amjad) cites a tartar inhibiting oral composition that includes a fluoride source, a dental abrasive, a carboxylate polymer and various phosphonic acids and their derivatives. A phosphated acrylic acid/hydroxyethyl methacrylate/alkyl methacrylic acid ester copolymer has been suggested in GB 2 139 635B (Causton) as useful in an oral composition for treating teeth.

Evident from the foregoing review of the art is the considerable effort expended to devise better tartar control compositions. By no means, however, has any of the reported art been able to more then attenuate the problem. There is considerable room for improvement over the known control agents.

Accordingly, it is an object of the present invention to provide a material of improved efficacy in controlling formation of tartar.

A still further object of the present invention is to provide a tartar control agent of improved taste, safety and appearance.

These and other objects of the present invention will become more apparent in light of the detailed description and Examples which follow.

SUMMARY OF THE INVENTION

An oral composition is provided comprising:

(i) a fluoride source present in an effective amount to reduce caries; and (ii) a polymer present in an effective amount to control build-up of tartar, said polymer having the formula I:

wherein A is a random polymeric residue comprising at least one unit of structure II,

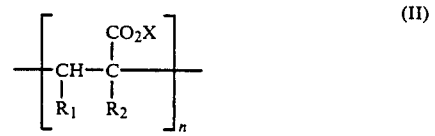

and at least one unit of structure III, different from a unit of structure II,

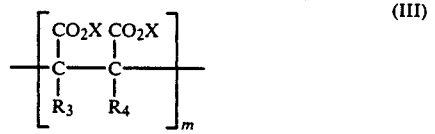

and B is hydrogen or a residue A; m and n are integers sufficient to provide polymer of weight averaged molecular weight ranging from about 400 to about 5000; m and n in residue A may each be the same or different from respective m and n in residue B; R is an—OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

DETAILED DESCRIPTION

Now it has been discovered that copolymers of, for example, acrylic acid and maleic acid (and other carboxylic monomers) whose structure is modified to include mono- or disubstituted hypophosphite units along the polymer backbone are effective antitartar agents. These materials are different in structure from typical acrylate/maleate copolymers in two respects. First, as noted they contain phosphite or hypophosphite groups. Secondly, they are of unusually low molecular weight. Materials with this structure are superior, as shown by in vitro and in vivo tests, to polyacrylates such as disclosed by Benedict et al. in U.S. Pat. No. 4,661,341 or polymaleates disclosed by Gaffar et al. in U.S. Pat. No. 4,183,914.

Based upon the herein disclosed studies, it is necessary that the polymers of this invention have three essential components. There must be present a monocarboxylic acid monomer, a dicarboxylic acid monomer, and a hypophosphite, which when reacted will form polymers of this invention. Absent any of these components, the resultant polymers will not be as effective.

The general structure of the polymers of this invention are as follows:

wherein A is a random polymeric residue comprising at least one unit of structure II,

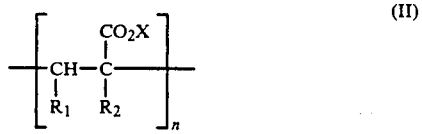

and at least one unit of structure III, different from a unit of structure II,

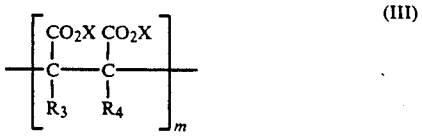

and B is hydrogen or a residue A; m and n are integers sufficient to provide polymer of weight averaged molecular weight ranging from about 400 to about 5000; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

Polymers forming the structure II will have a single carboxylic acid or salt group. There will be anywhere from 3 to 7 carbon atoms for this structure. Suitable monomers include acrylic acid, methacrylic acid, alpha-substituted alkyl acrylic acids, and beta-carboxyalkyl acrylates.

Monomers that form structure III will have at least two carboxylic acid groups and may range from 4 to 7 carbon atoms in size. Suitable monomers include maleic acid, fumaric acid, itaconic acid, mesaconic acid, citraconic acid, their anhydrides or salts.

Specific salts of the mono- and di- carboxylic monomers may be those including the counterions of sodium, potassium, calcium, strontium, zinc, copper, ammonium, $C_2$-$C_9$ alkanolammonium, $C_1$-$C_8$ alkyl amine and mixtures thereof. Strontium and zinc are particularly preferred counterions.

Most preferred are copolymers formed from acrylic acid and maleic acid.

Polymers of this invention are telomeric. Sodium hypophosphite is present in the polymerization medium to control molecular weight and to be incorporated into the backbone as mono- or disubstituted hypophosphite groups. These groups may be incorporated at the chain end or between monomer units in the chain. Typically, 70-90% of the total hypophosphite groups will be disubstituted. These groups are essential for the enhanced benefit of the polymers of this invention.

Molar ratio of total monomer to hypophosphite of the raw components before polymerization may range from about 40:1 to about 1:1, preferably from about 20:1 to about 4:1, optimally between about 16:1 to about 7:1. Lower ratios of monomer to hypophosphite generally result in lower polymer molecular weight and higher levels of incorporation of hypophosphite in the polymers.

Dicarboxylic monomers should be present in amounts in the copolymer ranging from about 10 to about 95 mole percent, preferably from about 20 to about 75 mole percent. Molar ratios of monocarboxylic monomer to dicarboxylic monomer should preferably be from about 5:1 to about 1:5, optimally between about 4:1 to about 1:1.

Polymers of this invention should have a molecular weight in the range between about 400 to about 5000, with a range of about 600 to about 2500 being preferred. These polymers will be present in the oral compositions in amounts ranging from about 0.01 to about 10% by weight, preferably about 0.4 to about 7%, optimally between about 1 to about 5%.

Carriers suitable for use with the polymers are preferably hydroxylic materials such as water, polyols and mixtures thereof. Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3-30% water, 0-80% glycerol and 20-80% sorbitol. Generally the amount of carrier will range from about 25 to 99.9% by weight, preferably from about 70 to 95% by weight.

When the oral compositions are in the form of a toothpaste or gel there will typically be included a natural or synthetic thickening agent in an amount from 0.1-10%, preferably about 0.5-5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive. Abrasives may be selected from water-insoluble alkali or alkaline earth metal salts of metaphosphate, calcium carbonate, aluminates and silicates. Especially preferred are silicate, dicalcium phosphate and calcium carbonate. Amounts of the abrasive will range from about 5% to about 80% by weight.

Adjunct tartar control agents, especially those containing phosphorous, may be combined with the polymers of the present invention. Inorganic phosphorous adjuncts may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as adjuncts include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavours that are usually present in the oral compositions are those based on oils of spearmint and peppermint. Examples of other flavoring materials include menthol, clove, wintergreen, eucalyptus and aniseed. Flavours may range in concentration from 0.1 to 5% by weight.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers for example Gantrez S-97 ®, and anti-gingivitis actives.

The following examples will more fully illustrate the embodiments of this invention. All parts, percentages and proportions referred to herein and in the appended claims are by weight of the total composition unless otherwise stated.

EXAMPLE 1

Copolymers of acrylic acid and maleic acid were prepared using sodium hypophosphite to promote telomerization. In a typical reaction, sodium hypophosphite monohydrate of a desired amount was added to deionized water and the solution heated to about 90°–100° C. Maleic anhydride was added to the solution and pH adjusted to about 4. Sodium or potassium persulfate (1–10% of total monomer feed) was used to initiate the polymerization. Acrylic acid at the appropriate ratio was added periodically over a 2–4 hour time period. Polymerization was continued until substantially 100% conversion was obtained.

Table I summarizes the materials prepared using the above procedure with comparison of key parameters.

TABLE I

| Sample | Acrylate/Maleate Ratio | Monomer/Hypophosphite Ratio | Molecular Weight |
|---|---|---|---|
| AM-A | 1:0* | 25:1 | 6000 |
| AM-B | 1:0* | 8:1 | 1600 |
| AM-C | 1.5:1 | 8:1 | 1200 |
| AM-D | 1.5:1 | 16:1 | 2100 |
| AM-E | 1.5:1** | — | 4600 |

TABLE I-continued

| Sample | Acrylate/Maleate Ratio | Monomer/Hypophosphite Ratio | Molecular Weight |
|---|---|---|---|
| AM-F | 4:1 | 8:1 | 1400 |
| AM-G | 2:1** | — | 2600 |
| AM-H | 2:1 | 32:1 | 4400 |
| AM-J | 2:1 | 16:1 | 2300 |

*Samples A and B have no maleate in the reaction medium or in the product.
*Samples E and G have no hypophosphite in the reaction medium or in the product.

The following materials listed in Table II were tested in similar assays for comparative purposes.

TABLE II

| Sample | Supplier | Composition | Molecular Weight |
|---|---|---|---|
| Sokalan CP5 | BASF | 4:1 Acrylic acid/Maleic acid | 70,000 |
| Sokalan CP7 | BASF | 2:1 Acrylic acid/Maleic acid | 50,000 |
| PA25PN | BASF | Polyacrylic acid | 4,000 |
| Belclene 201 | Ciba-Geigy | Polymaleic acid | 1,000 |
| Gantrez S-97 | GAF | 1:1 Maleic anhydride/methyl vinyl ether | 70,000 |

EXAMPLE 2

Rat Calculus Assay

The polymers of this invention were tested in vivo using a rat calculus assay. In this test, litters from Sprague-Dawley pregnant female rats (ex Charles River) were weaned (21 days old), weighed, tagged and split into cells of 25 animals balanced by gender and diet (consisting of 50% cornstarch, 32% nonfat powdered milk, 5% cellulose flour, 5% sucrose, 3% liver powder, 1% cottonseed oil, 2.7% sodium phosphate, 1% calcium chloride dihydrate, and 0.3% magnesium sulfate) with filtered city water. Subjects were treated with test solutions twice a day for three weeks. At the end of the test period, the teeth were scored in a blind protocol using a modified Frances & Briner method (J. Dental Res. 48(6) p. 1185–94 1969). A Nikon Stereoscopic Microscope was used for the evaluation (20x magnification).

The samples were prepared as rinse formulations. One hundred fifty microliters (150μL) of rinse was delivered to each subject using a 1 cc syringe. Deionized water with no agent added was used as the control sample.

The results of the tests are shown in Table III for several polymers including one of the polymers of the invention (AM-C). The term % inhibition is used as a measure of the reduction in calculus found on the teeth relative to the control sample.

TABLE III

| Results from the In Vivo Rat Calculus Trial | |
|---|---|
| AGENT | % REDUCTION |
| Gantrez S-97 | 2% |
| AM-A | 6% |
| Sokalan CP5 | 10% |
| Belclene 201 | 21% |
| AM-C | 29% |

The results indicate that significant reduction in calculus is found for the 1.5:1 acrylic acid/maleic acid copolymer containing substituted hypophosphite groups (AM-C). In addition, this sample give higher scores than other comparative polymers, including Sokalan CP5 (described in EP 321,650A), which has similar composition but higher molecular weight and no hypophosphite groups, and several which have appeared in the related art and are known antitartar agents (Belclene 201, described in U.S. Pat. No. 4,183,914; and Gantrez S-97, described in U.S. Pat. No. 4,627,977).

EXAMPLE 3

Microbial Mineralization

Several polymeric materials, including AM-C, were assessed using an in vitro microbial mineralization assay. Standard glass stirring rods are placed in an aqueous solution containing *Streotococcus mutans*, one of the microbes found in the human oral cavity. Microbes are allowed to grow onto the rods for about 2 days, and the rods are removed from the solution and placed in a treatment solution containing antitartar agents at levels of about 5 wt%. Treatment with a solution containing only deionized water is used as a control. After treatment for about 30 seconds, the rods are placed in a calcifying solution made up of calcium and phosphate at levels of 1.5 mM and 5.0 mM, respectively. The calcifying solution is supplemented with human saliva (about 25%). The glass rods are mineralized in the calcifying solution for 4 days, after which the level of calculus formation is assessed via calcium and phosphorus analysis. Results are calculated by comparing the % reduction of calculus formation to that of the control. Table IV contains results of the experiments.

TABLE IV

Results from In Vitro Microbial Assay*

| Treatment | % Reduction |
| --- | --- |
| Gantrez S-97 | 4 |
| Sokalan CP5 | 10 |
| Sokalan CP7 | 19 |
| Polyacrylate (PA25PN) | 45 |
| Polymaleate (Belclene 201) | 65 |
| AM-C | 65 |

*All agents tested at 1.25% level

The results in Table IV indicate that copolymer AM-C was more effective in reducing microbial growth and subsequent calcification than each of the polymers tested, except for Belclene 201, which was about equal in activity. The importance of molecular weight can be demonstrated, since the two materials having MW in the preferred range of this invention give the best activity.

TABLE V

Results from In Vitro Microbial Assay*

| Treatment | % Reduction |
| --- | --- |
| AM-D | 57% |
| AM-E | 31% |
| AM-F | 62% |
| AM-J | 49% |

*All agents tested at 1.25% level

Antitartar performance of other copolymers within the invention is outlined in Table V. From Table V it is evident that the copolymers which have molecular weights within the preferred range and which contain hypophosphite groups have greater efficacy in the assay.

EXAMPLE 4

Brushite Transformation Assay

Brushite (20 mg) of surface area $3m^2/g$ from Albright & Wilson which was free of stabilizers was suspended in 5ml of 0.25M imidazole buffer at pH 7.4 and incubated at 33° C. Agents were added to the buffer solution at desired levels and tested for their ability to inhibit the transformation of brushite to hydroxyapatite. The hydrolysis of the brushite (transformation) was followed by measuring the increase in supernatant phosphate in the buffer solution at 6 and 24 hours. The phosphate level was determined using the method of Chen et al. (Anal. Chem. 8, 1756 (1956)). Untreated brushite was used as the control. Table VI shows results from tests using a series of polymeric agents.

TABLE VI

Results From the In Vitro Transformation Assay

| Agent | Concentration | % Inhibition 6 hrs | % Inhibition 24 hrs |
| --- | --- | --- | --- |
| AM-C | 1 ppm | 100 | 8 |
| " | 2 ppm | 100 | 100 |
| " | 3 ppm | 100 | 100 |
| Belclene 201 | 1 ppm | 96 | 16 |
| " | 2 ppm | 96 | 57 |
| " | 3 ppm | 95 | 95 |
| PA25PN | 1 ppm | 56 | 4 |
| " | 2 ppm | 100 | 48 |
| " | 3 ppm | 100 | 100 |
| AM-B | 1 ppm | 5 | 3 |
| " | 2 ppm | 75 | 4 |
| " | 3 ppm | 97 | 11 |
| AM-G | 1 ppm | 5 | 0 |
| " | 2 ppm | 55 | 0 |
| " | 3 ppm | 99 | 0 |
| " | 5 ppm | 97 | 100 |
| AM-H | 1 ppm | 13 | 0 |
| " | 2 ppm | 61 | 0 |
| " | 3 ppm | 99 | 0 |
| " | 5 ppm | 100 | 80 |
| Gantrez S-97 | 1 ppm | 17 | 20 |
| " | 2 ppm | 16 | 8 |
| " | 3 ppm | 24 | 0 |

As shown in Table VI, copolymer AM-C performs more effectively as a transformation inhibitor than other polymers such as polyacrylate (PA25PN) or polymaleate (Belclene). The level of agent required to give about 100% inhibition for 24 hours is lower for AM-C than for the other agents. As in previous results, the criticalities for maximum efficacy appear to be the presence of acrylate, maleate, and substituted hypophosphite in the polymer, and molecular weights in the range of 500–2000. For example, higher molecular weight polymers with all three components (AM-H, MW=4400) are not as effective. Low molecular weight materials with no hypophosphite groups (AM-G) are ineffective as well.

EXAMPLE 5

Seeded Crystal Growth Inhibition Assay Combinations with zinc and Strontium

Combinations of the polymers of this invention with zinc and strontium salts were also tested in vitro using a Seeded Crystal Growth Inhibition Assay. This assay involved the treatment of synthetic hydroxyapatite (HAP) with a potential antitartar agent. The treated HAP was incubated at 37° C. in a calcifying solution made up of calcium and phosphate at 1.5mM and 4.5mM, respectively. The samples were filtered to remove any calcium phosphate crystals and the free calcium in the filtrate was measured using Atomic Absorption Spectroscopy. The percent inhibition was calculated as follows:

$$\% \text{ Inhibition} = \frac{[\text{Ca}] \text{ depletion from control} - [\text{Ca}] \text{ depletion from sample}}{[\text{Ca}] \text{ depletion from the control}}$$

This % inhibition is a measure of the degree of inhibition of calcium phosphate precipitation.

Table VI lists results of the seeded crystal growth inhibition experiments. The term "synergy" is used to demonstrate the enhanced effect of the polymer/zinc-strontium combination over the two individual components. For example, in the 1% polymer/0.1% zinc pairing the expected result from the combination would be (10%+50%)=60% inhibition; the actual value was 87%, resulting in a synergy of (87%−60%)=+27.

TABLE VII

| Zinc Combinations | | | |
|---|---|---|---|
| 1.5:1 acrylate/maleate* (8:1 monomer/hypophos.) (wt. % in water) | Zn(acetate)$_2$ (wt. % in water) | % Inhibition | Synergy |
| 1% | — | 10% | — |
| — | 0.1% | 50% | — |
| 1% | 0.1% | 87% | +27 |
| — | 0.2% | 45% | — |
| 1% | 0.2% | 80% | +25 |
| 2:1 acrylate/maleate** (16:1 monomer/hypophos.) (wt. % in water) | Zn(acetate)$_2$ (wt. % in water) | % Inhibition | Synergy |
| 1% | — | 12% | — |
| — | 0.1% | 50% | — |
| 1% | 0.1% | 92% | +30 |
| — | 0.2% | 45% | — |
| 1% | 0.2% | 87% | +30 |
| Strontium Combinations | | | |
| 1.5:1 acrylate/maleate* (8.1 monomer/hypophos.) (wt. % in water) | SrCl$_2$ (wt. % in water) | % Inhibition | Synergy |
| 1% | — | 10% | — |
| — | 0.2% | 0% | — |
| 1% | 0.2% | 78% | +68 |
| — | 0.5% | 0% | — |
| 1% | 0.5% | 79% | +69 |
| 2:1 acrylate/maleate** (16:1 monomer/hypophos.) (wt. % in water) | SrCl$_2$ (wt. % in water) | % Inhibition | Synergy |
| 1% | — | 12% | — |
| — | 0.5% | 0% | — |
| 1% | 0.5% | 77% | +65 |

*Sample AM-C
**Sample AM-J

Results found in Table VII indicate that synergistic increases in inhibition occur for combinations of the polymer with zinc and strontium salts.

Although this invention has been described with reference to specific examples, it will be apparent to one skilled in the art that various modifications may be made thereto which fall within its scope.

What is claimed is:

1. An oral composition comprising:
   (i) a fluoride source present in an effective amount to reduce caries; and
   (ii) a polymer present in an effective amount to control build-up of tartar, said polymer having the formula I:

wherein A is a random polymeric residue comprising at least one unit of structure II,

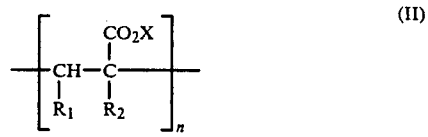

and at least one unit of structure III, different from a unit of structure II,

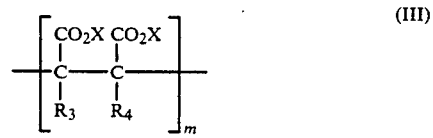

and B is hydrogen or a residue A; m and n are integers sufficient to provide polymer of weight averaged molecular weight ranging from about 400 to about 5000; m and n in residue A may each be the same or different from respective m and n in residue B; R is an—OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

2. A composition according to claim 1 further comprising a dental abrasive present in an amount from about 5% to about 80% by weight.

3. A composition according to claim 1 wherein the amount of fluoride ranges from about 0.005 to about 3%.

4. A composition according to claim 1 wherein the molecular weight of the polymer ranges from about 600 to about 2500.

5. A composition according to claim 1 wherein structure II is formed from monomers selected from the group consisting of acrylic, methacrylic, alpha-substituted acrylic, beta-carboxyalkyl acrylic acids or salts, and mixtures thereof.

6. A composition according to claim 1 wherein structure III is formed from monomers selected from the group consisting of maleic, fumaric, mesaconic, citraconic acid residues including their anhydrides or salts, and mixtures thereof.

7. A composition according to claim 1 wherein the polymer is present in amounts ranging from about 0.1 to about 10% by weight.

8. A composition according to claim 1 wherein the relative molar ratio of structure II to structure III ranges from about 5:1 to about 1:5.

9. A composition according to claim 8 wherein said molar ratio of structures II to III ranges from about 4:1 to about 1:1.

10. A composition according to claim 1 wherein the polymer is formed from a combination of acrylic acid or salt and maleic anhydride, its acid or salt and sodium hypophosphite.

11. A composition according to claim 10 wherein the molar ratio of total monomer to hypophosphite utilized to prepare the polymer ranges from about 40:1 to about 1:1.

12. A composition according to claim 11 wherein the molar ratio of total monomer to hypophosphite ranges from about 6:1 to about 7:1.

13. A composition according to claim 1 wherein at least some of X is zinc.

14. A composition according to claim 1 wherein at least some of X is strontium.

15. A method of controlling dental tartar which comprises treating teeth with a composition according to claim 1.

16. A method according to claim 15 wherein the composition is applied in the form of an aqueous mouth rinse.

17. A method according to claim 15 wherein the composition is incorporated into a dental paste and brushed onto the teeth.

* * * * *